United States Patent
Thompson et al.

(10) Patent No.: US 7,247,844 B2
(45) Date of Patent: Jul. 24, 2007

(54) INSTRUMENT AND METHOD TO FACILITATE AND IMPROVE THE TIMING ALIGNMENT OF A PET SCANNER

(75) Inventors: Christopher J. Thompson, Montreal (CA); Marie-Laure Camborde, Vancouver (CA)

(73) Assignee: Scanwell Systems, Montreal, Quebec (CA)

( * ) Notice: Subject to any disclaimer, the term of this patent is extended or adjusted under 35 U.S.C. 154(b) by 322 days.

(21) Appl. No.: 10/700,157

(22) Filed: Nov. 3, 2003

(65) Prior Publication Data

US 2007/0131857 A1    Jun. 14, 2007

Related U.S. Application Data

(60) Provisional application No. 60/424,520, filed on Nov. 7, 2002.

(51) Int. Cl.
*G12B 13/00* (2006.01)
*G01T 1/164* (2006.01)

(52) U.S. Cl. ................ 250/252.1; 250/363.03

(58) Field of Classification Search ............. 250/252.1, 250/363.03
See application file for complete search history.

(56) References Cited

U.S. PATENT DOCUMENTS

| 4,060,726 A | * | 11/1977 | Luitwieler et al. ....... 250/252.1 |
| 5,841,140 A | * | 11/1998 | McCroskey et al. ... 250/363.03 |
| 6,774,358 B2 | * | 8/2004 | Hamill et al. ............ 250/252.1 |

* cited by examiner

*Primary Examiner*—David Porta
*Assistant Examiner*—Shun Lee
(74) *Attorney, Agent, or Firm*—Ansel M. Schwartz

(57) ABSTRACT

A system for providing the timing alignment for a scanner. The system includes a removable source and detector assembly which is placed near the center of the scanner when in use. The source includes a long-lived positron emitting radioactive source. The radioactive source is in close contact with a fast plastic scintillator or other mechanism of detecting the ionization due to positron decay. A method for reading out the precise time at which the surrounding medium detects the ionization due to positron decay. A mechanism for using this time as a reference clock unto which the detectors in the scanner can be aligned.

14 Claims, 6 Drawing Sheets

12
INSTRUMENT AND METHOD TO FACILITATE AND IMPROVE THE TIMING ALIGNMENT OF A PET SCANNER

This application claims the benefit of U.S. Provisional Application No. 60/424,520 filed Nov. 7, 2002.

FIELD OF THE INVENTION

The present invention is in the field of medical imaging instruments that detect radiation emitted from a patient after the administration of a radioactive substance. More particularly, the present invention is in the field of calibrating instruments that detect this radiation.

BACKGROUND OF THE INVENTION

Many types of equipment are designed to detect physical events such as particle-matter interactions. Event detection is widely used in scientific research and in medicine. An example of useful event detection equipment is a nuclear medicine camera, also referred to as a Gamma camera. Such cameras can aid in locating diseased tissue, such as tumours, in the body.

Some conventional nuclear medicine imaging systems have two or more detectors. The detectors are of some of these are planar and include an array of detector devices such as photo multiplier tubes (PMTs). The detectors arrays are positioned above different sides of a patient. Gamma cameras can operate in different modes. For example, some nuclear medicine cameras perform single photon emission computed tomography (SPECT) in which information from a single detector is used to produce information. Other nuclear medicine cameras perform positron emission tomography (PET) in which the detection of two scintillation events, one in each of two detectors that occur 180.degree. apart, are used to compute imaging information. These instruments are called PET scanners. In a PET scanner, detectors detect scintillation events that result when each photon of a photon pair collides with a crystal. In common PET scanners, many detectors are arranged in a series of rings which surround the region of the patient's body being scanned.

Before a PET scan is performed, the patient is injected with a radio-pharmaceutical, such as Fluoro-deoxyglucose (FDG). The radio-pharmaceutical is labeled with fluorine-18 which emits positrons that interact with electrons in the body. As a result of the interaction, the positrons are annihilated and gamma rays, including photon pairs, result. Photon pairs leave the point of the interaction in directions of travel that are 180.degree. apart from each other. When a photon comes in contact with a crystal of a detector, a scintillation event occurs. The scintillation event is detected by a photo detector device of the detector creating analog information. The analog information is digitized and processed by electronics and software to produce image information about objects such as tumors in the body.

Typical PET scanners, include detectors with multiple devices such as PMTs. For various reasons, the propagation time of trigger signals indicating detection of events varies between PMTs. One factor contributing to propagation time variance is the fact the time taken for the two gamma rays to reach the detectors depends on the distance traveled by each, even though are created at the same time. Yet another factor is that PMTs vary physically in ways that affect their response times. Another factor is the variance in the length of cables used to carry signals associated with different PMTs. Yet another factor is crystal response time variance by area. If the trigger signal is received by processing hardware and software significantly later than the event detected, inaccuracies may result. Inaccuracies may include false detection indications, and images with poor resolution. Therefore, it is critical to calibrate the timing of trigger signals so that they portray, as accurately as possible, what is actually occurring in the tissue of the patient.

Proper calibration of trigger signals can be important in PET scanners. Commonly, the timing calibration is performed on PET systems by positioning a radioactive source between detectors and monitoring rates of coincident events. Normally, the sources are the same ones which are used to perform transmission scans which are used for attenuation correction in PET. These sources orbit around the patient close to the detectors. Since they are far from the center of the scanner, they are always much nearer one detector than the other. Therefore, the gamma ray must arrive at farther detector later than the one arriving at the nearer detector, since both travel at the speed of light. Prior methods of calibration are often time consuming, since the source is only between a particular pair of detectors for a very small fraction of the total time, and may be imprecise because the steps performed are not accurately repeatable.

Detector calibration is especially critical in PET. If the collision of one photon of a photon pair with one detector is not reported at almost the same time as the collision of the other photon of the photon pair with another detector, the coincident event will be missed. Usually a timing window is used to define the maximum time during which two gamma rays are detected, and are considered coincident. The width of this timing window, (normally denoted by the Greek letter tau, $\tau$) is of the order of 5–10 nsec. If the timing window is too wide, it is more likely that a random coincidence will occur. A random coincidence occurs when gamma rays from two different annihilations are detected within the timing window. Random coincidences occur between two detectors, I, and J having count-rates $N_I$ and $N_J$ respectively, at a rate given by:

$$R_{IJ} = 2\tau N_I N_J$$

Random coincidences are the main source of noise in PET studies performed at high count-rates. When the detectors are very well aligned the timing window may be narrowed, allowing higher activities to be administered, and shorter imaging times. Techniques currently exist for calibrating PET systems, but these techniques have several disadvantages. Current techniques are complex and not accurately repeatable. Current techniques perform the timing alignment using many sub-groupings of detectors. Initially two opposing groups are aligned, then the first of these groups is used to align a third, while the second group is used to align a forth. Subsequently, the third group is used to align a fifth group, and the forth group is used to align a sixth group and so on. This leads to a propagation of timing errors, since the fifth group and the sixth group are not aligned to primary reference. The timing window could be made narrower, if all detectors were aligned to a common reference source. In addition, current calibration operations take a relatively long time to perform.

SUMMARY OF THE INVENTION

A method and apparatus for performing the timing alignment of all detectors in a PET scanner with respect to a single centrally located source is described. The source is a positron emitting isotope with a long half live like germanium-68 or sodium-22. The source is surrounded with a detector which detects the ionization when the positron is emitted from the parent nucleus. The positron detector could be a piece of fast plastic scintillator coupled to a photo-multiplier, or it could be one or more avalanche photo-diodes and suitable amplifier(s). It is only after the positron has lost the kinetic energy with which it was ejected from the parent nucleus, that it can pair up with an electron and they subsequently annihilate to produce two gamma rays which travel in opposite directions.

Using the source, the time differences for all detectors would be compared to the one stationary central source. The source is contained in a medium which detects the ionization caused by the energy which the positron must lose before it annihilates. In the present implementation of this invention, the radioactive isotope is germanium-68, and it is deposited in the centre of a cylinder of plastic scintillator. The plastic scintillator is coupled to a small photo-multiplier. The source could be sodium-22 (which has a longer half-life), and the detector could be a photo-diode (which would make it smaller).

One of the key points which makes the present invention non-obvious is that radioactive decay is a random process so it was not previously thought possible to provide a common "clock signal" to which to align the detector timing circuits using a radioactive source. It is impossible to predict when any particular atom will decay, all one can say with certainty, is that it will decay, and the time until it decays is related to the half-life which is a intrinsic property of each isotope. This invention "works" because positron decay is a two-step process. The new source detects the decay of the parent nucleus, and the scanner's conventional detectors detect the gamma rays which are the product of positron annihilation. One can make an analogy of a clock making a "tick-tock" sound, with the "tick" always preceding the "tock". The "tick" in this analogy, is the emission of a positron, and the "tock" is the emission of the gamma rays. In the prior art, the "tick" is not detected, instead, the calibration is done by listening for the "tock" and adjusting the timing delays so as to have two recorded at the same time. In the present invention, we can detect the "tick" and we know that the "tock" must occur a fixed time later (since all detectors are almost the same distance from the source, and the gamma rays travel at the speed of light).

One embodiment includes a single, centrally located, positron emitting source surrounded by a cylinder of plastic scintillator which is used to detect the ionization which occurs as the positron loses its kinetic energy before it can annihilate with an electron and subsequently annihilate. This plastic scintillator produces a light flash which is detected by a fast photo-multiplier tube. The signal from the photo-multiplier can be fed to a constant fraction discriminator, and serve as a reference signal which occurs before a gamma ray arising during the annihilation of this positron can be detected, by the surrounding detectors of the PET scanner.

BRIEF DESCRIPTION OF THE DRAWINGS

In the accompanying drawings, the preferred embodiment of the invention and preferred methods of practicing the invention are illustrated in which.

DETAILED DESCRIPTION

Figure 5:
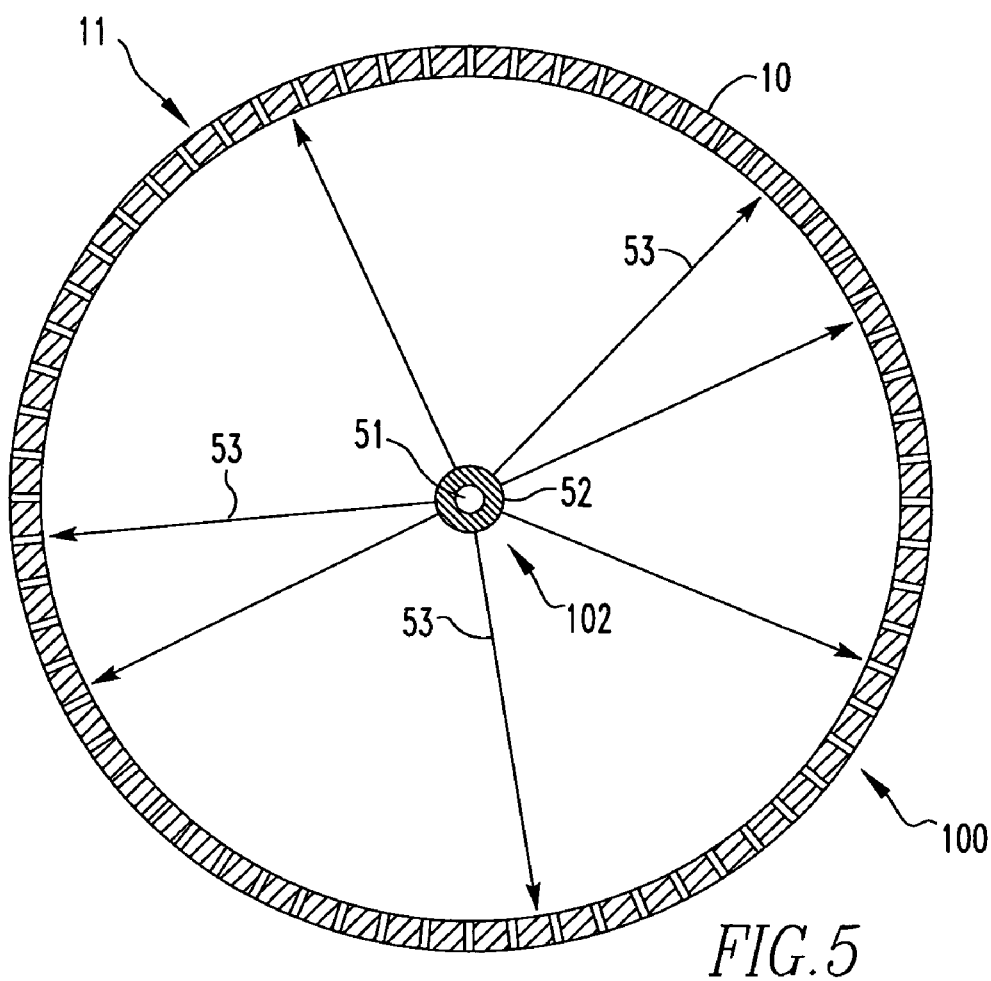
FIG. 5 is a diagram showing the disposition of source and detector in one embodiment.
Figure 7:
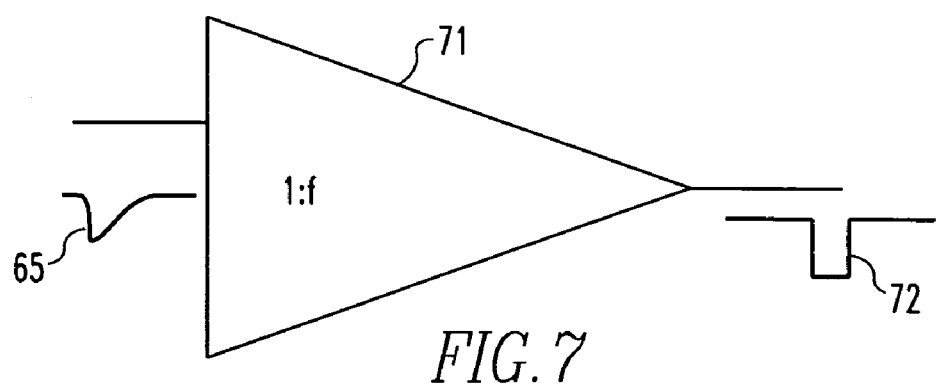
FIG. 7 is a circuit diagram of the trigger event detection circuitry of one embodiment.
Figure 6:
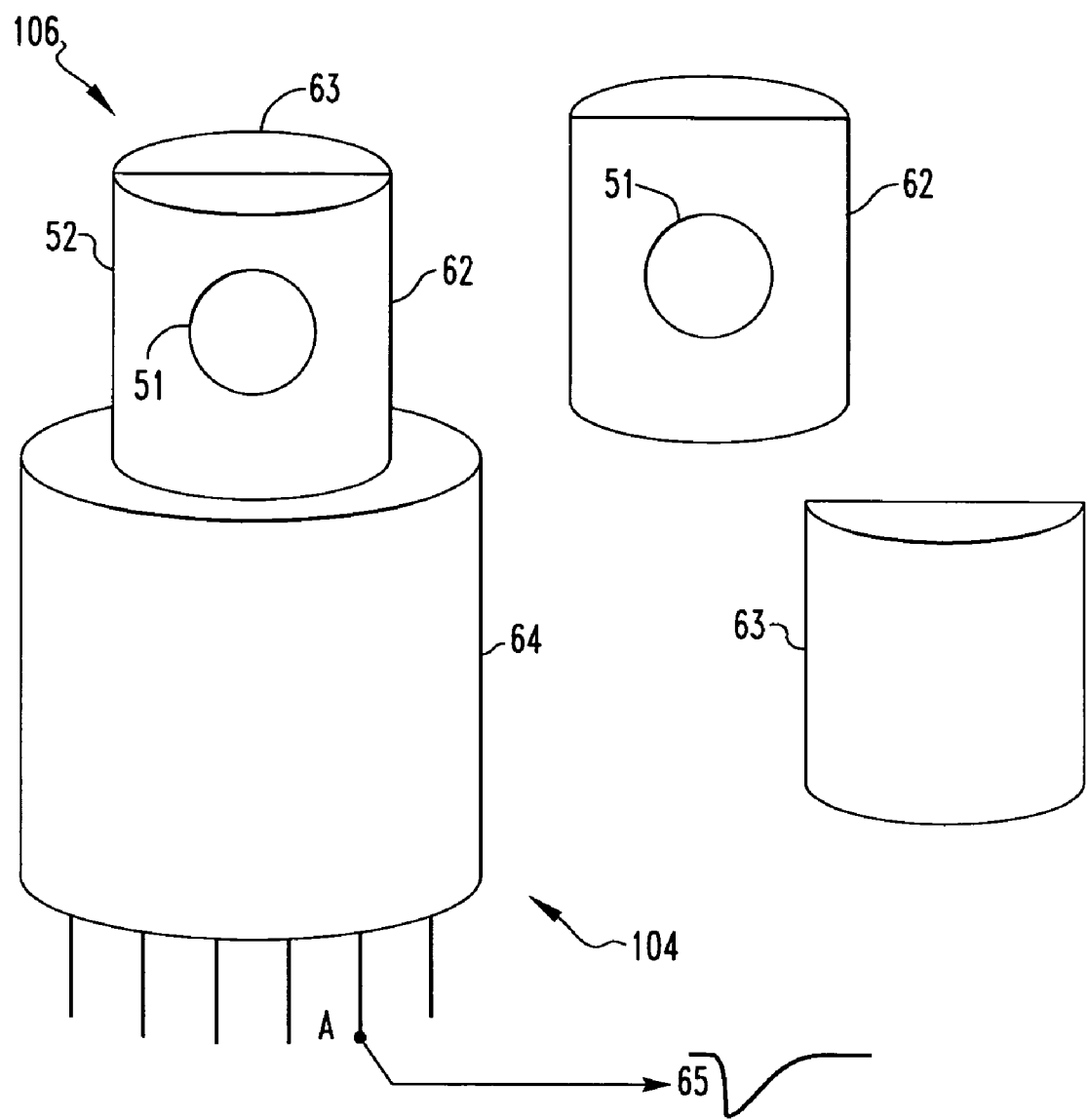
FIG. 6 is a diagram of the positron emitting source and surrounding plastic scintillator.

Referring now to the drawings wherein like reference numerals refer to similar or identical parts throughout the several views, and more specifically to FIGS. 5–7 thereof, there is shown a system 10 for time alignment of a scanner 100. The system 10 comprises a radioactive source 14. The system 10 comprises means 102 of detecting, and producing a signal at the time of radioactive decay of the source 51. The system 10 comprises means 104 of converting the signal into a common reference clock electronic timing signal for calibration of the scanner 100.

Preferably, the radioactive source 51 emits positrons and has a half-life longer than six months. The radioactive source 51 is preferably surrounded by a medium 106 capable of detecting when the source 51 decays by positron emission and before the positron combines with an electron and they annihilate subsequently producing two gamma rays which may be detected by the scanner's 100 detectors 11.

Preferably, the medium 106 is coupled to the means 104 of converting the detection into the electronic timing signal. The timing signal is preferably used as a timing reference for the scanner's 100 gamma ray detectors 11. Preferably, the timing reference serves as a system 10 clock during the timing alignment of all the detectors 11 such that they may all aligned to this common reference clock.

All the scanner's 100 gamma ray detectors 11 may be aligned simultaneously to the common system 10 clock. Preferably, the source 51 may remain stationary near the center of the scanner 100 during the alignment procedure, since the gamma rays are emitted isotropically.

Preferably, the source 51 includes a layer 51 of a positron emitting isotope. The source 51 preferably includes a cylinder 52 of plastic scintillator, and the layer 51 is placed on an inner surface of the cylinder. Preferably, the cylinder 52 comprises two pieces 62, 63 which are fixed together. The source 51 preferably includes a photomultiplier that is coupled to the two pieces 62, 63. Preferably, the photomultiplier has an anode output 65 which produces the signal whose amplitude is proportional to the positron energy each time a positron is detected.

The present invention pertains to a time alignment method for a scanner 100. The method comprises the steps of placing a radioactive source 51 in a generally central location in the scanner 100. There is the step of detecting, and producing a signal at the time of radioactive decay of the source 51. There is the step of converting the signal into a common reference clock for calibration of the scanner 100.

This system 10 eliminates the +/−2 nanoseconds error associated with an orbiting source 51, so provides a more precise time measurement.

This system 10 provides a common time reference "clock" to which all detectors 11 can be aligned.

All lines of response are calibrated for the entire period of the scan, and not only during the small fraction of the scan during which an orbiting source 51 is on the line of response.

Since all of the scanner 100's detectors 11 are about the same distance from the source 51, the travel time for all gamma rays is almost the same.

In the operation of the invention, a method and apparatus for independently calibrating an event detection array is described. One embodiment includes a centrally placed positron emitting source 51 surrounded by a plastic scintillation detector coupled to a single photo-multiplier tube (PMT), within an array for many gamma ray detectors which may be divided into multiple zones, or discrete detectors sometimes referred to as "blocks". A calibration circuit calibrates delays of the trigger signals of all detectors simultaneously, by acquiring events in apparent coincidence counts for a few seconds from any of the PET detectors and the central source for many different delay times without the necessity of moving the radioactive source.

Figure 1:
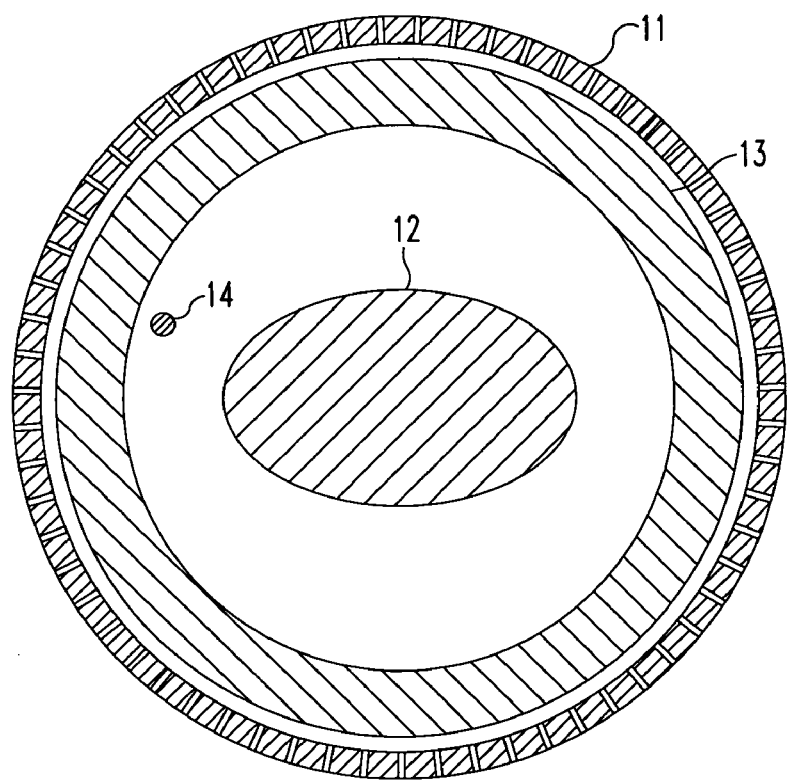
FIG. 1 is a vertical section through the prior art calibration method.

FIG. 1 shows the prior art, and represents a vertical cross-section of a ring-type PET scanner, where rings of detectors 11 surround the patient section 12 being examined. In the prior art, during the calibration of the PET scanner, the source 14 used for performing transmission scans during patient examinations orbits the imaging field, just inside the slice defining septa and collimator 13.

Figure 2:
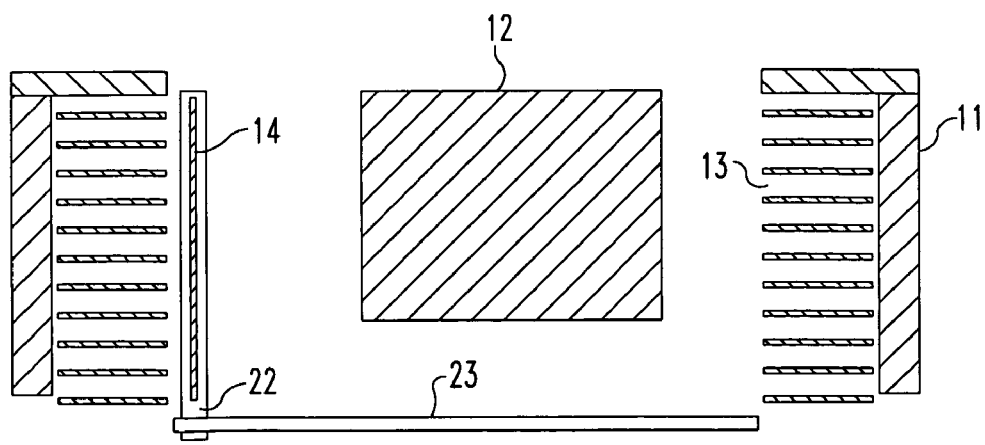
FIG. 2 is a horizontal section through the prior art calibration method.

FIG. 2 shows the prior art, and represents a cross-sectional view of a ring-type PET scanner, where rings of detectors 11 surround the patient section 12 being examined. In the prior art, during the calibration of the PET scanner, the source 14 used for performing transmission scans during patient examinations orbits the imaging field, just inside the slice defining septa and collimator 13. The rod source 14 is contained in a sleeve 22, which is attached to a mechanism 23, which allows it to orbit just inside the collimator 13 and be retracted when not in use.

FIGS. 1 and 2 represent the prior art, and are vertical and cross-sectional diagrams of one embodiment of nuclear medicine imaging system, such as PET scanner with detectors disposed in annular rings 11 about the patient section being examined 12. The PET scanner represented here could be an already existing PET scanner, such as, for example the ECAT HR+ manufactured by CTI in Knoxville Tenn. Between the patient body section, and the detector arrays, are a pair of dense, annular end-plates, and a set of thin dense annuli 13, known as septa. Just inside the septa is one (or more) rods of positron emitting material 14, which is (are) used for performing transmissions scans. In the prior art, this, (these) source(s) is (are) also used to perform the timing alignment which is the subject of this invention. The source (s) may be retracted and inserted into the scanning field, and when inserted is (are) disposed move in an orbit by means of a rotating mechanism 23.

Figure 3:
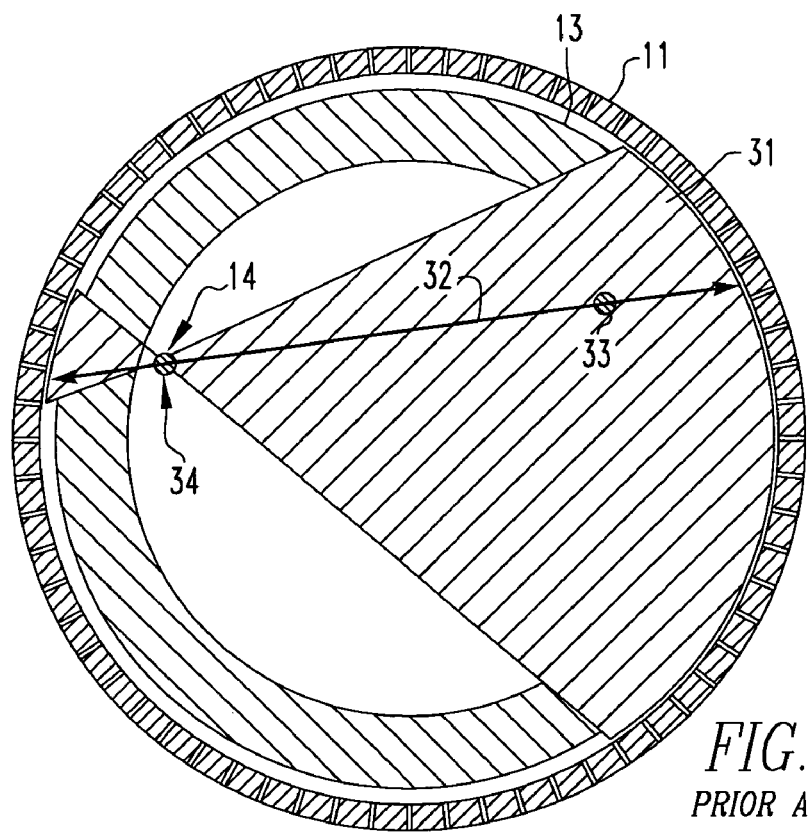
FIG. 3 is a vertical section through the prior art showing the limited number of detectors.

FIG. 3 shows the prior art, and represents a vertical sectional view of a PET scanner. It is only the "fan" detectors, 31, whose timing calibration can be performed while the source is in this position. PET detectors 11 are arranged in rings. The lead septa which are in place during timing calibration 13 are situated just inside the detector ring. The source(s) 14 system calibration orbit the patient just within the inner surface of the septa.

Figure 4:
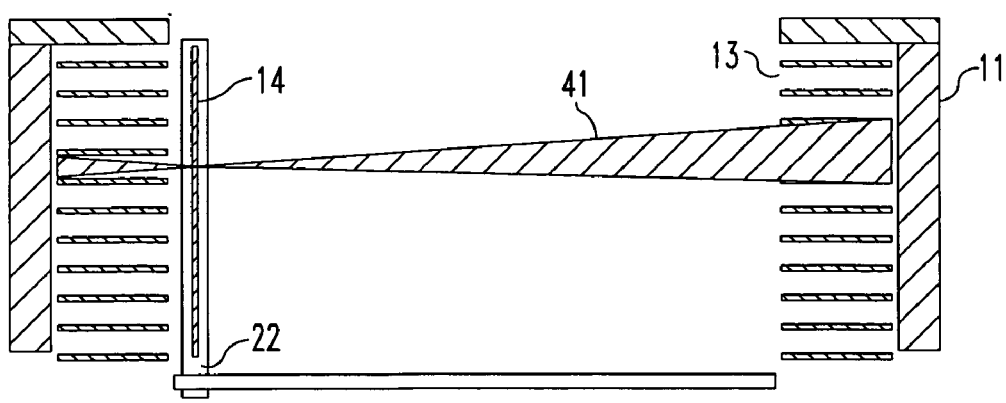
FIG. 4 is a horizontal section through the prior art showing the limited number of detectors.

FIG. 4 shows the prior art, and represents a cross-sectional view of PET scanner showing the detectors 11 slice-defining septa 13, positron emitting source used calibration 14, source holder 22, and source rotating mechanism 23. Only groups of the detectors within "fan" 41 can have their timing alignment measured with the source in this position.

FIGS. 3 and 4 represent the prior art, and are vertical and cross-sectional diagrams of one embodiment of nuclear medicine imaging system, such as PET scanner which show all the lines of response which are collinear with the source used for performing the timing alignment and the transmission scans when the orbiting source, 14, is in the position shown. In a one example of a PET scanner, the CTI ECAT HR+, there are 320 detectors, each with 64 crystals, sometimes called "blocks", disposed on the surface of a cylinder consisting of four rings. It is only when the source is on the line joining a pair of these crystals 32 that true coincident counts can be recorded. Since the source diameter in the prior art is less than the detector width, this occurs only twice in each revolution, in positions 34 and 33, (or about 2/640 of the total time the measurement is being made). This small fraction of the available time during which the timing calibration information can be obtained, makes the timing calibration a very slow process.

FIG. 5 shows one embodiment of the present invention in which the PET detectors 11 surrounding a centrally located positron emitting source 51, which is introduced into the aperture of the PET scanner for the purpose of performing the timing calibration, and removed during normal patient scanning. The source, emits positrons which are detected by the surrounding plastic scintillator 52, before they annihilate. The gamma rays 53, emitted each time a positron annihilates, are subsequently detected by one of the detectors in the detector array 11.

FIG. 5 shows the preferred embodiment of the present invention, in that there is one, centrally located, positron emitting source 51, which is completely surrounded with plastic scintillator 52. The source is almost the same distance from all detectors 11, so all lines 53 from the source to the detectors are almost the same length. Thus, for all of the gamma rays resulting from positron annihilation in the plastic scintillator, traveling at the speed of light, will arrive at the detectors is almost exactly the same. This source 51 is placed within the detector array only during the calibration procedure. It could be inserted by a mechanical means on command prior to starting the calibration procedure described later, or it could be inserted manually.

The sources can be plated or painted on the surface scintillator, and in that case, there would be no need to hollow the cylinder out, since the thickness is negligible. However, had the source been made by absorbing the radioactivity onto a ceramic substrate in the form of a small cylinder 1 mm in diameter and 1 mm long, then this was inserted in a hole in the cylinder. The cutting of the cylinder along its axis would be preferable as the light detection would be more uniform, and independent of the direction of the positron emission.

The photomultiplier is a Hamamatsu R1635 (it was chosen because it is both fast and small: Fast is clearly essential for this application, and small could be very useful to minimize the overall size of the source-PMT assembly to store it when not being used). The plastic scintillator is from Alpha Spectra Inc. of Grand Junction, Colo., called ASI-200. It is made of polyvinyltoluene. It has a rise time of 0.9 nsec and a decay time of 2.1 nsec, and produces 10,000 light photons per MeV.

The scintillation light goes out isotropically just like any light, but there is a reflector round the scintillator to get as much light as possible into the photomultiplier, as is well known in the art. A common reflector to use is the Teflon tape which is in all plumbing supply stores for wrapping pipe threads. In the PET literature this is often referred to as "plumber's teflon tape".

FIG. 6 shows one embodiment of the present invention in which the timing alignment source 51 consists of a thin layer of a positron emitting isotope like germanium-68, which is plated on the inner surface of a cylinder of plastic scintillator 52, which has been cut into two pieces 62, 63. In this illustration, the two pieces are formed by cutting the cylinder along its axis perpendicular to a diameter of one of its circular ends. There could be other possible arrangements, such as cutting it along a diameter approximately half way along its length. The two pieces are then glued together with optical cement, and coupled to a fast photo-multiplier 64. The anode of the photo-multiplier 64 produces a signal, whose amplitude is proportional to the positron energy, each time a positron is detected.

FIG. 6 shows one embodiment of the timing calibration source, in which a positron emitting source 51 is plated, coated, or otherwise attached to an inner surface of a cylinder of plastic scintillator 52, which was previously cut in two pieces 62, 63, which were subsequently rejoined with optical cement. The cylinder could be cut either horizontally or vertically. The important criterion is that the positrons emitted by the source lose all their energy in the plastic scintillator. The plastic scintillator, 52, is coupled with optical cement to a fast photo-multiplier 64, the anode output 65, of which is used to identify the time precise time at which the parent nucleus decayed by positron emission.

The prongs on the back of the photo-multiplier are the contact points to its internal electrodes. (It is a vacuum tube and looks quite like the tubes in an old radio.) One of the contact pins is the anode connection, and that is the one marked. The anode of the photomultiplier is connected using a coaxial cable to the input of the constant fraction discriminator. The cable can be quite long (about 20 feet long). The cable could be connected to a point which is internal to the gantry on the scanner. However, there are other scanners which have this section of their electronics external to the scanning gantry, and could be in a separate room.

FIG. 7 shows the signal 65 from the anode of the photo-multiplier 64, which is fed into a constant fraction discriminator 71, which produces a short logic pulse 72 at precisely the same time after each input signal reaches a certain faction, f, of its peak value.

FIG. 7 shows the output signal 65 from the anode of the photo-multiplier 64, which is fed into a constant fraction discriminator 71, which produces a short logic pulse 72 at precisely the same time after its input signal reaches a certain faction, f, of its peak value. Constant fraction discriminators, similar to the Model CF8000 manufactured by Ortec Inc. of Oak Ridge, Tenn., are commonly used in most PET scanners. Since the excess mass of the parent nucleus and the daughter nucleus plus positron is distributed randomly between the daughter nucleus and the positron, the amplitude of the anode signals can take on any value between zero and the energy corresponding to the mass difference. For accurate timing, one must use a constant fraction discriminator, rather than a fixed energy threshold to obtain a precise timing signal.

Figure 8:
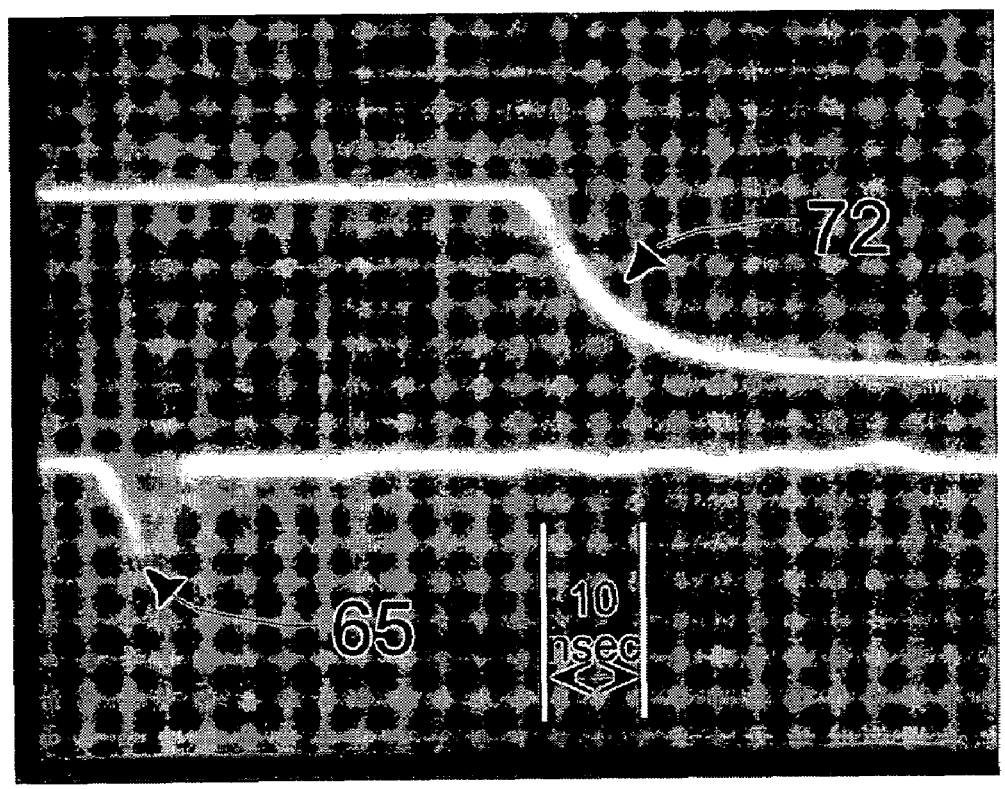
FIG. 8 shows input and output signals from the positron-decay detector in one embodiment.

FIG. 8 shows time exposure photograph of oscilloscope tracings of the anode signals arising from each of many positrons losing energy in plastic scintillator 52, which is used to initiate a timing measurement. Each of these signals 65 may be if different amplitude, which makes upper trace, containing many signals, look blurred. These pulse are much faster than those from the conventional inorganic scintillators used to detect the gamma rays. The output signals 72 from the constant fraction discriminator is shown above the input signal 65. The time scale: 10 nanoseconds/division.

FIG. 8 shows an oscilloscope tracing showing anode signal 65 from the photo-multiplier 63 from plastic scintillator 65, which is used to initiate a timing measurement. This pulse is much faster than that from the conventional inorganic scintillators 52 used to detect the gamma rays. The output signal 72 from the constant fraction discriminator is shown above. The time scale in this image is 10 nanoseconds/division. The measurement depicted in FIG. 8 was made with an oscilloscope whose bandwidth was only 150 MHz, so the rise time of the display is actually limited by the oscilloscope's rise time.

Figure 9:
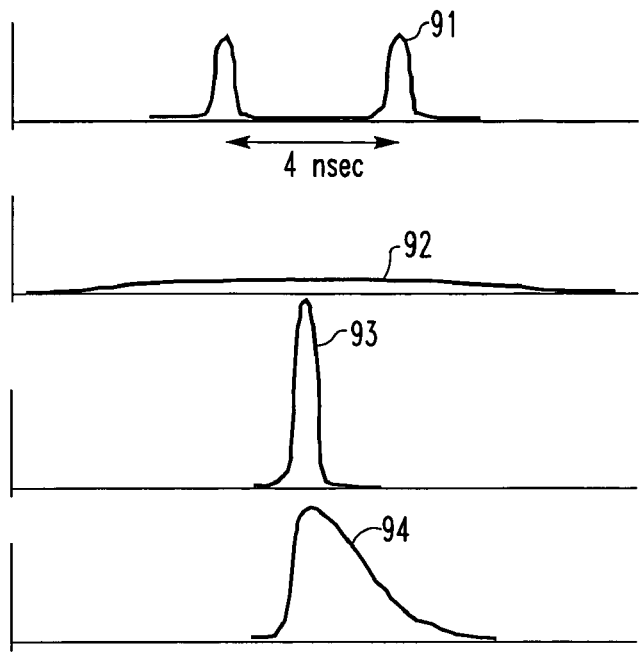
FIG. 9 shows timing spectra of an ideal detectors, the prior art and one embodiment.

FIG. 9 shows the timing spectra for one line of response, plotting number of counts vs arrival time difference, which would be obtained in the case of "plastic scintillators with much higher stopping power" 91, typical BGO detectors used in PET scanners 92, one central source, and "ideal" gamma ray detectors 93, and a central source, and a typical BGO detector 94.

FIG. 9 shows a set of simulated timing spectra for one line of response. A timing spectrum is obtained by plotting the time difference between the occurrence of pairs of related events. These spectra can be obtained using commonly available instruments such as a Canberra 1443A time to amplitude converter and a multi-channel analyzer such as a Tracor Model TN1705. These simulated spectra could be obtained by plotting number of counts vs arrival time difference, which would be obtained in the case of "very fast detectors with very high stopping power" 91, typical BGO detectors used in PET scanners 92, one central source, and "ideal" gamma ray detectors 93, and a central source, and a typical BGO detector 94. The upper trace 91, shows that very fast, high stopping power detectors, would produce twin peaks in the timing spectrum for any line of response, since the line of response is only traversed when the source is either near one end or the other. In typical PET scanners, the source orbits at a diameter of about 60 cm. Since the speed of light is close to 30 cm/nsec., the time difference is either +2 or −2 nsec. The second trace 92 shows the same timing spectrum acquired with typical BGO detectors in a PET scanner. BGO detectors are much slower than plastic scintillator, (300 nsec vs <1 nsec., so the timing spectrum is much more blurred. The third trace 93, shows how the timing spectrum from a centrally located positron emitting source would appear as detected by ideal gamma ray detectors. There is only one peak, of twice the amplitude of the upper trace 91, since all the gamma rays now travel the same distance. The lowest trace 94 shows the appearance of the timing spectrum between a plastic scintillator and a slower PET detector. All of these spectra are shown as smooth curves, without any statistical noise, which would make the peaks much less conspicuous that depicted here, unless the measurement were made over a very long time. They are shown without noise to illustrate the relative magnitudes and disposition of the peaks. It will be appreciated by those skilled in the art, statistical noise is always present in this kind of measurement due to the random nature of radioactive decay, and the need to complete the timing calibration in timely manner.

Figure 10:
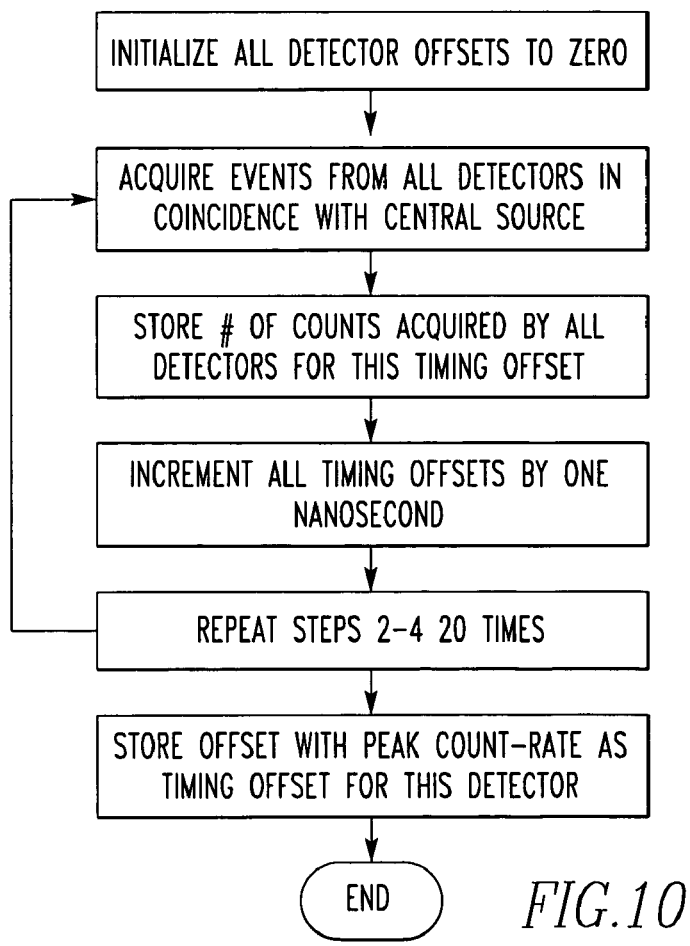
FIG. 10 is a flow diagram showing steps of one embodiment of a timing calibration operation.

FIG. 10 shows a block diagram of the steps required to obtain the timing alignment of all detectors in the PET scanner with respect to a common central positron-decay triggered central source.

FIG. 10 shows the method in order to perform the timing calibration using the source described in the previous figures. It represents a block diagram of the steps required to obtain the timing alignment of all detectors in the PET scanner with respect to a common central positron-decay triggered central source. This process starts with the initialization all the timing offsets to a common negative value with respect to the trigger pulses from the central positron-triggered source. Recordable events occur when the central positron-triggered source produces a timing pulse which is in apparent coincidence with one or two of the PET detectors. Events which are in apparent coincidence are then counted for a period which may be vary from a few seconds to about one minute. The timing offsets for all crystals are then incremented by a short time, for example, one nanosecond. Many, about 20, such sets of recordable events are acquired. Each data set consists of the number of apparently coincident counts acquired for each crystal for each timing offset. In the case of a PET scanner with 320 "blocks" of 64 crystals each, and 20 different time delays, this represents a 320×64×20 (409600) array. This array can be considered as 20480 data sets, one for each crystal. Each of these data sets consists of 20 bins each of which contain the number of counts acquired by one crystal in apparent coincidence with the central positron-emitting source. Each data set should represent the timing spectrum and will contain one peak. The location of this peak represents the timing offset for this crystal.

All PET scanners function by recording the near simultaneous arrival of pairs of 511 keV gamma rays which result from the annihilation of a positron and an electron. They do not detect positrons directly. These gamma rays are detected by arrays of detectors which surround the subject being imaged. In order to assure that a pair of gamma rays is truly from the same positron annihilation, the maximum times difference between the two gamma ray detections is kept as small as possible. However if this difference is too small, some genuine gamma ray pairs will be ignored. This will occur if the positron was much nearer to one detector, so the travel time for the gamma ray to the near detector is shorter than that to the far detector. It could also be that the cables connecting the pair of detectors are of different lengths, so again the times would be different. It could also be that inevitable noise and or drift in the electronics, make the arrival times uncertain. An important step in the initial setting up of a PET scanner, and part of its on-going maintenance, is the calibration of the timing circuits so that when gamma rays do arrive in coincidence at the detectors, they are correctly recognized as such, and are used to form an image, and those which are not in coincidence are rejected. This system is a different way to perform the timing calibration which is faster and more accurate than previous techniques.

As stated above, PET scanners do NOT detect positrons, but coincident gamma rays. The present invention includes a device in the PET scanner which DOES detect positrons, and use the information from this extra component to calibrate the timing of the conventional detectors of the scanner. When a radioactive atom decays by positron emission the positron is ejected from the nucleus with considerable energy. It is well known that this energy must be lost in the surrounding medium before it can interact with an electron and annihilate. It is also well known that this loss of energy in the surrounding medium can be detected, and this is used in imaging techniques like autoradiography (in which thin slices of tissue from a recently euthanized animal are laid on an X-ray film and expose the film according to the amount of radioactive material adjacent to the film). In the present invention, this energy is captured in a piece plastic scintillator, which converts the kinetic energy of the positron into light. This takes place before the positron annihilates with an electron and their mass is converted into two 511 keV gamma rays. The light from plastic scintillator is emitted very rapidly after the energy is absorbed by atoms in the plastic. The light flash (lasting only a few hundred picoseconds) is converted to an electrical signal by coupling the plastic scintillator to a fast photo-multiplier. This combination of positron emitting radioactive source in intimate contact with a plastic scintillator, which is optically coupled to a photo-multiplier serves as a "trigger source" with which to align the PET scanner's detectors.

This trigger source is placed near the center of the PET scanner during the calibration procedure. In order to calibrate the timing circuits, using this technique. The scanner is set up to detect the positron decay trigger signals from the central trigger source which are in apparent coincidence with the gamma rays which are detected by the scanner's gamma rays detectors in the conventional way. If the timing circuits are perfectly aligned, many coincidences will be detected between the trigger source and any of the detectors. If they are poorly aligned, only very few events will be detected, and these only by chance.

The method of this invention comprises making multiple acquisitions during which the events involving all detectors in apparent coincidence with the trigger source are counted, and between which the timing delay for all detectors is changed slightly. The number of counts collected in bin (corresponding to a specific delay) are compared. The time bin with the highest number of counts recorded by any detector represents the time delay with which signals for that detector should be offset. These offsets, one for each detector, are then stored in a table for use during conventional PET scans.

There are several key points in which this technique differs from current practice, which make it intrinsically faster and more precise.

1) All detectors are timed with respect to a common source, the central trigger-source. Since there is only one trigger source, errors introduced by calibrating some time delays with respect to one detector and others with respect to an other, and so on, and then trying to align the groups are eliminated.
2) Since the source is centrally located, the time taken for gamma rays to travel to each of the PET detectors is almost the same, so this time can be measured more precisely than if the source is moving beyond the periphery of the scanner's field of view as current practice.
3) Since the central trigger-source is in full view of all detectors, it can be used to calibrate all detectors simultaneously. If the source is moving, as in current practice, it can only calibrate pairs of detectors, the lines joining which are collinear to it at any time. This allows more counts to be recorded in a given time, shortening the total time required for system calibration.

In recent years, PET scanners have become recognized as the most specific non-invasive imaging method for the diagnosis and staging of cancer. Other, more mature imaging modalities such as X-ray computed tomography (CT) and Magnetic Resonance Imaging (MRI) can acquire images of patient sections rapidly, so that a typical scan takes only a few minutes to perform. PET scans have traditionally taken much longer, since the detectors and their associated circuits must acquire and analyze many more (typically 100 times more) unpaired gamma ray detections than pairs of gamma rays which are in true coincidence. This limits the amount of radioactivity which can be injected into the patient. If there are too few counts, the image quality is poor, and if there are too many, the random counts contaminate the image, and again its quality is poor. Faster detectors made of Lutetium oxy-orthosilicate (LSO) are being used in modern PET scanners to make them faster and one would expect to the random count-rate by reducing the coincidence resolving time, $\tau$. However, even though the scintillation decay time of LSO is over 10 times shorter than that of BGO, the value of $\tau$ can only be reduced from about 8 to 6 nsec. One of the controlling factors which prevents the resolving time being reduced further, is the ability to perform the timing calibration sufficiently precisely. Typically, this is now done using the orbiting source which is primarily intended for performing transmission scans, and results in a timing window that must be 4 nsec longer than if a central source were used. Thus a technique, such as that described herein has a great advantage in allowing modern, fast, PET scanners to function optimally with higher injected activities. This would provide improved image quality, and shorter scan times. In turn, this would lead to improved patient throughput, allowing more patients to be scanned with this highly accurate imaging technique.

Another reason for using longer coincidence resolving time is the possibility of drift in the timing circuits, and the time needed to perform the calibration. It is not practical to perform a timing calibration while the scanner is un-attended, as can be done with the "blank scan" used with attenuation correction. If timing stability is a factor, the source could be extended and retracted as needed, allowing un-attended daily timing calibrations.

The technique has been described in the context of a ring-type PET scanner, but the same concept would be equally valuable in other types of scanner. Some instruments use a pair of gamma cameras with thicker than normal crystals and no perforated lead collimators. These are often divided into overlapping zones with quasi-independent electronics. Each of these zones could be aligned to a single central source, just as the blocks in a ring-type scanner. Other scanners use an array of flat panels with pixilated scintillation detectors. These detectors are also divided into overlapping zones with quasi-independent electronics, and could all be aligned to a single central source.

Embodiments have been described which provide a method and apparatus for independently calibrating detectors for many types of PET scanners. Embodiments described include particular arrangements in a system, such one using circular arrays of detectors. Certain other trigger signal and surrounding detector systems are also shown and described. However, numerous variations can be made upon these arrangements without departing from the spirit and scope of the claimed invention.

With reference to the claims, for instance, in one embodiment the radioactive source can be Germanium-68; the means of detecting, and producing a signal at the time of radioactive decay of the source can be the plastic scintillator and photo-multiplier; and the means of converting the signal into a common reference clock for calibration of the scanner can be the constant fraction discriminator.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A time alignment system for a scanner comprising:
a radioactive source which decays by emitting positrons;
means of detecting the emission of a positron, and producing a signal at the time when the radioactive decay of the source decays by the emission of the positron; and
means of converting the signal into a common reference clock for calibration of the scanner.

2. A system as described in claim 1 wherein the radioactive source emits positrons and has a half-life longer than six months.

3. A system as described in claim 2 wherein the radioactive source is surrounded by the means of detecting and producing a signal when the positron is emitted, wherein the means of detecting and producing a signal is a medium capable of detecting when the source decays by positron emission and before the positron combines with an electron and they annihilate subsequently producing two gamma rays which may be detected by the scanner's detectors.

4. A system as described in claim 3 wherein the medium is coupled to means of converting the detection into an electronic timing signal.

5. A system as described in claim 4 wherein the timing signal is used as a timing reference for the scanner's gamma ray detectors.

6. A system as described in claim 5 wherein the timing reference serves as a system clock during the timing alignment of all the detectors such that they may all aligned to this common reference clock.

7. A system as described in claim 6 wherein all the scanner's gamma ray detectors may be aligned simultaneously to the common system clock.

8. A system as described in claim 7 wherein the source remains stationary near the centre of the scanner during the alignment procedure, since the gamma rays are emitted isotropically.

9. A system as described in claim 8 wherein the source includes a layer of a positron emitting isotope.

10. A system as described in claim 9 wherein the medium is a cylinder of plastic scintillator, and the layer is placed on an inner surface of the cylinder.

11. A system as described in claim 10 wherein the cylinder comprises two pieces which are fixed together.

12. A system as described in claim 11 wherein the means of converting the detection into an electronic timing signal is a photomultiplier that is coupled to the two pieces.

13. A system as described in claim 12 wherein the photomultiplier has an anode output which produces the signal whose amplitude is proportional to the positron energy each time a positron is detected.

14. A time alignment method for a scanner comprising the steps of:
placing a radioactive source which decays by emitting positrons in a generally central location in the scanner;
detecting the emission of a positron, and producing a signal at the time when the radioactive decay of the source decays by the emission of the positron; and
converting the signal into a common reference clock for calibration of the scanner.

* * * * *